United States Patent
Huang et al.

(10) Patent No.: US 8,528,384 B2
(45) Date of Patent: Sep. 10, 2013

(54) METHOD OF DETERMINING SURFACE PORE MOUTH DIAMETER DISTRIBUTION OF POROUS MATERIAL

(75) Inventors: Yan Huang, Jiangsu (CN); Jian Yu, Jiangsu (CN)

(73) Assignee: Nanjing University of Technology, Nanjing, Jiangsu (CN)

( * ) Notice: Subject to any disclaimer, the term of this patent is extended or adjusted under 35 U.S.C. 154(b) by 390 days.

(21) Appl. No.: 13/119,722

(22) PCT Filed: Nov. 3, 2009

(86) PCT No.: PCT/CN2009/074768
§ 371 (c)(1),
(2), (4) Date: Mar. 18, 2011

(87) PCT Pub. No.: WO2010/072104
PCT Pub. Date: Jul. 1, 2010

(65) Prior Publication Data
US 2011/0167897 A1    Jul. 14, 2011

(30) Foreign Application Priority Data
Dec. 23, 2008  (CN) .......................... 2008 1 0244140

(51) Int. Cl.
*G01N 15/08* (2006.01)
(52) U.S. Cl.
USPC .......................................................... 73/38
(58) Field of Classification Search
USPC .................................. 73/38, 64.47
See application file for complete search history.

(56) References Cited

U.S. PATENT DOCUMENTS

| 4,644,779 | A  | * | 2/1987  | Sisti et al. ......................... 73/38 |
| 4,744,240 | A  | * | 5/1988  | Reichelt ............................. 73/38 |
| 5,425,265 | A  | * | 6/1995  | Jaisinghani ....................... 73/38 |
| 6,568,282 | B1 | * | 5/2003  | Ganzi ......................... 73/861.42 |
| 6,684,685 | B2 |   | 2/2004  | Gupta et al. |
| 6,789,410 | B1 | * | 9/2004  | Gupta et al. ...................... 73/38 |
| 2004/0206161 | A1 | * | 10/2004 | Gupta et al. ...................... 73/38 |
| 2004/0255646 | A1 |   | 12/2004 | Smiricinschi |

FOREIGN PATENT DOCUMENTS

| CN | 2509578 Y | 9/2002 |
| CN | 101435763 A | 5/2009 |
| WO | PCT/CN2009/074768 | 7/2010 |

* cited by examiner

*Primary Examiner* — Hezron E Williams
*Assistant Examiner* — Nathaniel Kolb
(74) *Attorney, Agent, or Firm* — Global IP Services; Tianhua Gu

(57) ABSTRACT

The invention relates to a method for the determination of the pore-mouth size distribution at the surface of porous materials. (i) While the backside of the sample is purged with a gas, the sample is immersed into a liquid wetting agent. (ii) The gas pressure is gradually decreased, and the gas flowrate is monitored; or, the gas flowrate is gradually decreased, and the gas pressure is monitored. (iii) When the gas flow stops, the remaining pressure in the system corresponds to the largest pore-mouth size. (iv) The pore-mouth size distribution can be calculated through a "dry curve" and a "wet curve", which are curves of the gas flowrate vs. pressure at the dry and wetted states of the sample. The calculation of the pore-mouth size and the pore-mouth size distribution is the same as that based on the conventional bubble point method. The measurement of the pore-mouth size of the porous materials is of great importance when they are used as the substrates for surface coatings.

2 Claims, 6 Drawing Sheets

METHOD OF DETERMINING SURFACE PORE MOUTH DIAMETER DISTRIBUTION OF POROUS MATERIAL

CROSS REFERENCE TO RELATED PATENT APPLICATION

The present application is the US national stage of PCT/CN2009/074768 filed on Nov. 3, 2009, which claims the priority of the Chinese patent application No. 200810244140.8 filed on Dec. 23, 2008, which application is incorporated herein by reference.

BACKGROUND OF THE INVENTION

1. Field of the Invention

The present invention relates to a method to determine the pore size distribution on the surface of porous materials. In particular, this method measures the size of the pore-mouth rather than that of the pore-throat (i.e., the narrowest position) in the pore tunnels.

2. Related Art

Because of their internal porosity, porous materials have been widely applied in industries (such as petrochemistry, food, construction, metallurgy, aerospace, etc.) for separation and purification, gas distribution, catalysts, noise silencing, shock absorption, shielding, heat exchange, electrochemistry, and so on. One important use of porous materials is as porous membranes with symmetric or asymmetric structure. In recent years, attention has been paid to the concept of composite membranes, which consist of a functional membrane layer on a substrate material. For filtration, the membrane pore size is very significant. Here the term "pore size" mainly refers to the narrowest position in a pore tunnel, i.e., the "pore-throat", as shown in FIG. 1. In contrast, the "pore-mouth" means the mouth of a pore on a surface. This is more important for coatings on the surface of the porous material (in most of the cases, the pore-throat is significantly smaller than the pore-mouth), and a typical example is the fabrication of palladium composite membranes.

Palladium membranes (including palladium alloy membranes) are highly permeable to hydrogen and have been applied to hydrogen purification for several decades. Except for hydrogen and its isotopes, no other gases can pass through the membranes. The commercialized membranes are self-stand ones with a thickness of around 100 μm or larger. Although it is highly desired to reduce the membrane thickness, to which the membrane permeability is inversely proportional, reduction is limited by the poor physical strength of the membrane and the manufacturing cost. An ideal solution is the introduction of a composite membrane concept, i.e., deposition of a thin layer of palladium or palladium alloy on a porous substrate (e.g., porous ceramics and porous stainless steel), whereby the membrane thickness can be decreased to a couple of microns. Accordingly, the membrane permeability can be increased by one order of magnitude, and the consumption of the noble metal is also decreased. However, a challenging problem is the appearance of membrane defects. The larger the pore-mouth of the substrate material, the thicker the membrane has to be. To fabricate a palladium membrane that is completely pinhole-free, particular attention must be paid to the largest pore and, more specifically, the largest pore-mouth of the substrate [Yu J, Hu X, Huang Y. Ceramic modifications of the porous stainless-steel surface toward the Palladium membranes for hydrogen separation. Prog. Chem., 2008, 20(7/8): 1208-1215.].

There are many techniques for the determination of the pore size distribution of a porous material [Hernández A, Calvo J, Prádanos P, Tejerina F. Pore size distributions of track-etched membranes; comparison of surface and bulk porosities. Colloids Surf. A, 1998, 138: 391-401.] [Zhang Q, Zhang Z, Wei H. Characterization methods of porous material filter rating. Filter & Separator, 2000, 10: 33-37.], such as mercury intrusion porosimetry, the bubble point method, liquid-liquid displacement, suspension filtration, and gas permeation. Mercury intrusion porosimetry probes the pore size distribution via monitoring the volume of mercury that the sample absorbs at different pressures. This method, however, also detects the blind pores, which are not significant for filtration. Therefore, the results may not be consistent with the real filtration effects. Moreover, mercury intrusion porosimetry is not suitable for a membrane with asymmetric structure.

The principle of the bubble point method is as follows [ASTM F316-2003 Standard test methods for pore size characteristics of membrane filters by bubble point and mean flow pore test.] [ISO 4003-1990 Permeable sintered metal materials determination of bubble test pore size.] [GB/T 1967-1996 Test method for pore diameter of porous ceramics.] [GB 5249-1985 Permeable sintered metal materials; Determination of bubble test pore size.] [Huang P, Xing W, Xu N, Shi J. Pore size distribution determination of inorganic microfiltration membrane by the gas bubble pressure method. Technology of Water Treatment, 1996, 22: 80-84.]. When a pore tunnel is blocked with a wetting agent, a certain pressure is necessary for a gas to reopen the pore tunnel because of the surface tension of the wetting agent, and the smaller the pore size, the larger the gas pressure that will be required. Therefore, an increase in the gas pressure will successively reopen the pore tunnels with decreasing pore size. The first pore to be reopened is the largest, i.e., the "bubble point". This method works by measuring the gas flowrate versus pressure at the dry and wetted states of the sample, and the pore size distribution can then be calculated according to a theoretical model. Noticeably, the pore size given by the bubble point method actually refers to the "pore-throat". In most of the cases, the shape of the pore tunnel is irregular, and the so-called "pore size" actually refers to the diameter of a circle whose area is the same as the cross-sectional area of the pore-throat.

The principle of the liquid-liquid displacement is the same as that of the bubble point method, except that the gas is replaced with a liquid that is insoluble in the wetting agent. This method also probes the pore-throat size.

To measure the pore size through suspension filtration, a filtration of a suspension containing spherical solid particles is performed under laminar flow, and the size distribution of the particles remaining in the suspension is analyzed before and after filtration. The largest pore size of the filter is determined by the diameter of the largest particle that passes through the filter. The definition of the pore size given by this method refers to the diameter of an inscribed circle at the pore-throat. For a non-circular pore-throat, its size measured through suspension filtration will be smaller than that given by the bubble point method.

Except for mercury intrusion porosimetry, all of the above methods provide the pore-throat size distribution, which is important for filtration performance study. However, none of them probe the pore-mouth size distribution, and, so far, there have been no good solutions. Direct observation by microscopy (for example, SEM) can be considered in laboratory studies, but it is limited by the small visual field and generally only applicable for small specimens. Moreover, the direct microscopic observations cannot locate the largest pore-mouth of the whole sample quickly.

SUMMARY OF THE INVENTION

The present invention is a method for the determination of the pore-mouth size distribution of porous materials.

The technical solution of the present invention is as follows. While a porous sample is being purged from its backside with a compressed gas, the sample is immersed into a wetting agent. When the gas pressure decreases, the smallest pore-mouth will be firstly closed by the wetting agent, and the last to be closed is the largest pore-mouth. By the difference between the curves of the gas flux vs. gas pressure at the dry and wetted states of the sample, the pore-mouth size distribution can be calculated. Both this method and the conventional bubble point method work through the relationship between the pore size and the capillary surface tension of the wetting agent. Namely, the conventional bubble point method works through the relationship between the pore size and the force to reopen the pore by a gas, while this method works through the relationship between the pore size and the force to close the pore with a liquid. The principle of data processing is the same for the two methods, but the conventional bubble point method measures the pore-throat while this method measures the pore-mouth. For the conventional bubble point test, the sample is fully wetted in advance, and the gas pressure is then gradually increased to study the pore-opening. With this method, the sample must be purged by a compressed gas before immersion in the wetting agent, and the gas pressure is gradually decreased to study the pore-closing effect.

The capillary force p generated by the wetting agent at the pore-mouth is [Liu P, Ma X Ed. Techniques for characterization of the porous materials. Beijing: Metallurgical Industry Press, 2006: 60-61.]

$$p = \frac{4\gamma\cos\theta}{d} \quad [1]$$

where $\gamma$ is the surface tension of the wetting agent, $\theta$ is the contact angle, and d is the diameter of the pore-mouth. $\theta$ is close to 0 when the sample can be perfectly wetted by the wetting agent. As soon as a pore-mouth is closed, the gas pressure P=p, i.e., $$d \approx \frac{4\gamma}{P} \quad [2]$$

If the static pressure of the wetting agent is considered, Equation [2] should be changed to $$d = \frac{4\gamma}{P - \rho g h} \quad [3]$$

where $\rho$ is the density of the wetting agent, g is a constant of 9.8 N/kg, and h is the depth of the sample in the wetting agent. However, in practice, the sample is immersed shallowly, and the static pressure $\rho g h$ is negligible against the gas pressure.
Technical Operation The operation of the method described in the present invention comprises:

(i) Purging the sample from its backside with a compressed gas and then immersing the sample into a liquid wetting agent.
(ii) Gradually decreasing the gas pressure and monitoring the gas flux to obtain the curve of the gas flux vs. pressure. When the bubbling completely stops (i.e., the gas flux becomes zero), the corresponding gas pressure refers to the largest pore-mouth. For convenience of description, this curve is denoted as the "wet curve", and, accordingly, the curve obtained with the dry sample without the wetting agent treatment is denoted as the "dry curve". Alternatively, the wet and dry curves can be obtained by monitoring the gas pressure following a decrease in the gas flux.
(iii) Calculating the pore-mouth size distribution according to the wet and dry curves. To calculate the mean pore-mouth size, a "half-dry curve" is plotted with the data of the "dry curve" but halving each gas flux value. The pressure corresponding to the intersection point between the "wet curve" and the "half-dry curve" gives the mean pore-mouth size. The mean pore-mouth size may be more precisely described as the "mid-flux pore-mouth size", which means that the pores with pore-mouths above and below this size contribute equally to the total flux.

Obviously, the dry curve can be obtained by either increasing or decreasing the gas pressure. Although the dry and wet curves can be obtained by either monitoring the gas flux as a function of pressure or vice versa, the latter option was found to be even more convenient in practice.

The porous materials that are suitable for testing include ceramics, glasses, metals, plastics, or their composites. The gas used in the measurements is preferably air, nitrogen, or argon. The wetting agent should be chemically inert, non-toxic, and with low viscosity and perfect wettability for the porous materials. Because an initial gas pressure has to be set to start recording the wet curve, the following factors should be considered: the estimated pore-mouth size, the surface tension coefficient of the wetting agent, the maximum scale values of the pressure and flowrate devices, the pressure of the gas resource, and so on. Equation [2] shows that the pore-mouth size is inversely proportional to the critical gas pressure. Namely, the smaller the pore mouth, the higher pressure necessary to prevent the pore closure upon contact with the wetting agent. Taking a wetting agent of anhydrous ethanol ($\gamma=22.3\times10^{-3}$ N/m) as an example, a pore-mouth of 0.5 µm will start to close when the gas pressure decreases down to 0.18 MPa, while a pore-mouth of 0.05 µm corresponds to a gas pressure of 1.78 MPa. The higher the initial gas pressure, the smaller the pore-mouth size that can be detected. However, too high an initial gas pressure causes a waste of time and gas. In practice, extremely small pores often contribute negligibly to the gas flux. Therefore, the initial pressure does not need to be very high. In addition, a wetting agent with low surface tension efficient (such as an alcohol or ketone) is also a good choice. The initial gas pressure is preferably 0.2-0.5 MPa, and it is suggested to use specific wetting agents such as Galden HT230, Porewick, Galwick, Silwick, and so on. Water is a preferable wetting agent for testing a hydrophilic material with a pore-mouth diameter of 5-200 µm. In cases where the pore-mouth size of the sample cannot be estimated, a certain initial gas pressure can be tried. If it is not sufficient, a higher gas pressure or other wetting agent can be tried after drying the sample.

Whether using the conventional bubble point method or this method, the basic testing data are the wet and dry curves, by which all of the results (such as the largest pore size, the mean pore size, the most probable mean pore size, and the pore size distribution) are calculated. In most cases, the largest pore-mouth size and the mean pore-mouth will be the most important. Neither the mathematical model nor the calculation method is within the scope of the present invention, and the details are available in the literature [Huang P, Xing W, Xu N, Shi J. Pore size distribution determination of inorganic microfiltration membrane by the gas bubble pressure method. Technology of Water Treatment, 1996, 22: 80-84.].

Advantages of the Invention

1. The conventional methods for pore size tests (such as the bubble point method, liquid-liquid displacement, and suspension filtration) can only measure the pore-throat, while the method described in the present invention detects the pore-mouth size, which is an important factor for surface coatings.

2. The direct measurement of the pore-mouths by means of microscopy is not effective because the visual field is small and it is difficult to locate the largest pore-mouth in the whole sample. Thus, this method is more feasible.

3. The device associated with the present invention is similar to that for the conventional bubble point method, and it is easy to construct and operate.

EMBODIMENTS

Embodiment 1

(i). The sample to be tested was a porous ceramic sheet with a diameter of 30 mm and a thickness of 2 mm. It was successively cleaned with diluted HCl solution (HCl 37%, 1 ml/L) and water each for about 5 min, followed by drying.

Figure 1:
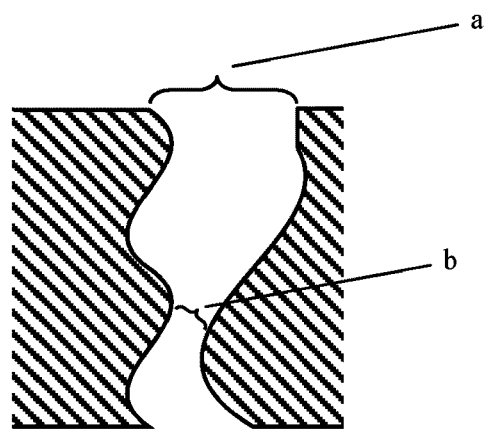
FIG. 1 is a schematic of the pore-throat and pore-mouth of a pore tunnel in a porous material. (a) Pore-mouth. (b) Pore-throat.
Figure 2:
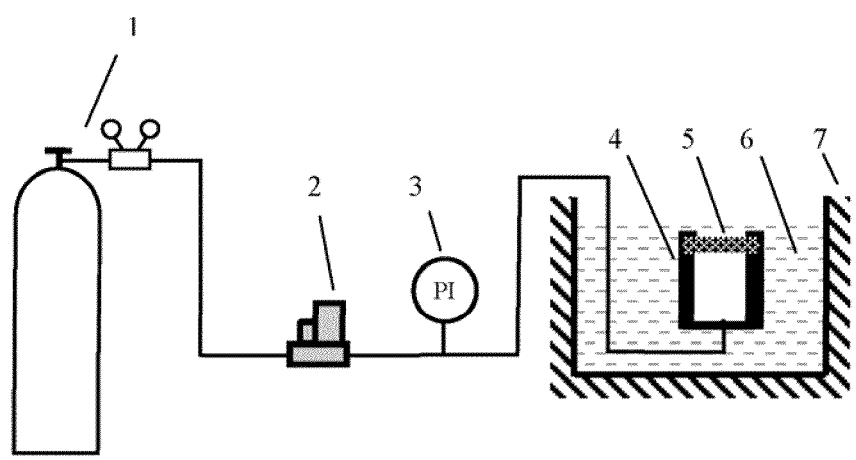
FIG. 2 shows a testing device for sheet samples. 1. Gas cylinder, 2. Mass flow controller, 3. Pressure gauge, 4. Testing cell, 5. Sample, 6. Wetting agent, 7. Tank.
Figure 4:
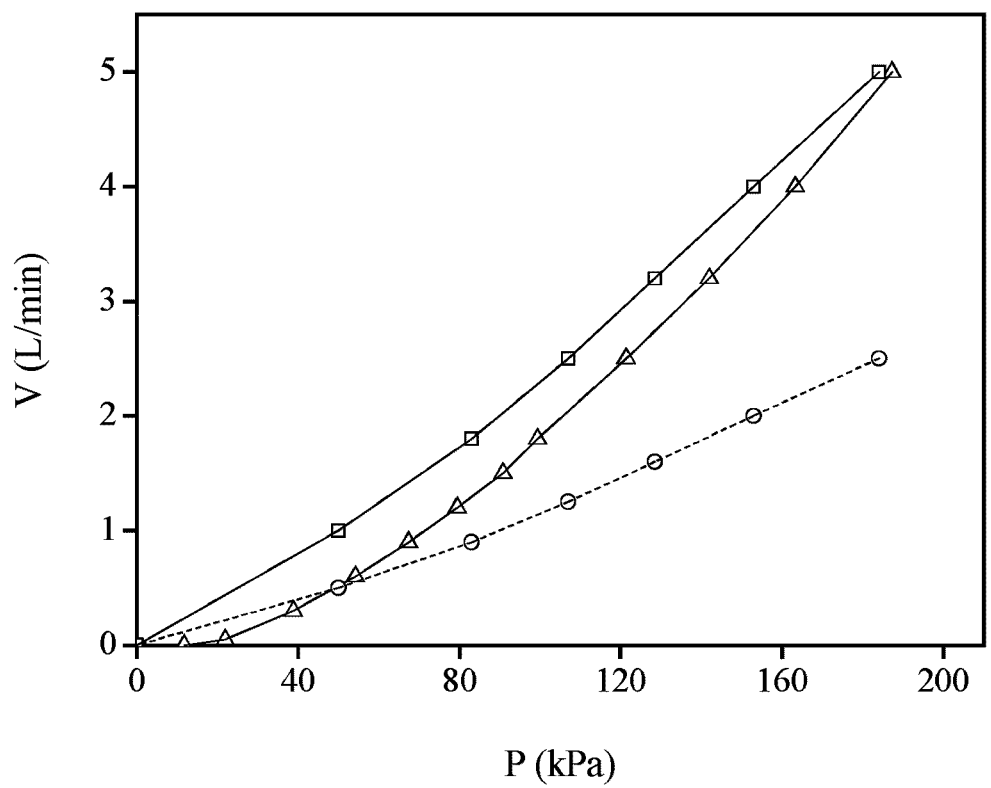
FIG. 4 shows the gas flux vs. pressure curves for a porous ceramic sheet.

(ii). The testing device, as illustrated in FIG. 2, consisted of a nitrogen gas cylinder (1), a mass flow controller (2), a pressure gauge (3), a testing cell (4), and a tank (7). The sample (5) was placed into the testing cell (4) and sealed by two silicone rubber gaskets (o.d., 30 mm; i.d., 10 mm; thickness, 2 mm). The nitrogen was fed with the mass flow controller (2), and the nitrogen flowrate vs. pressure was recorded until the nitrogen flowrate reached 5 L/min, which corresponded to a nitrogen pressure of 184 kPa. The dry and half-dry curves were then plotted and are shown in FIG. 4.

(iii). The water ($\gamma=72.9\times10^{-3}$ N/m) in the tank (7) was used as the wetting agent (6), and the testing cell (4) was immersed into the water (6) below 1-2 cm, while the nitrogen flow through the mass flow controller (2) was continued. The testing cell (4) was slightly shaken so that the sample surface could sufficiently contact the water, and the pressure gauge (3) read a value of 187.3 kPa. When the nitrogen flowrate was decreased to 4 L/min, the pressure became 163.3 kPa. With a decrease in the nitrogen flowrate, the pressure in the system was recorded. When the bubbling pores became very few, the nitrogen was completely switched off, and the final pressure remained in the system (i.e., the "bubble point" pressure) was 11.2 kPa, corresponding to the largest pore-mouth size of 26 μm. The wet curve, as shown in FIG. 4, was plotted, and the intersection point of the wet and half-dry curves corresponds to a pressure of 45.6 kPa, providing a mean pore-mouth size of 6.4 μm according to Eqn. [2].

(iv). The pore-throat size of this sample was measured on a CFP-1100A porometer (PMI Inc., USA) with water as the wetting agent, and the mean and largest pore-throat sizes were 3 and 6.3 μm, respectively. Both are lower than the corresponding pore-mouth sizes, and this result coincides with the fact that the pore-mouth is larger than the pore-throat.

Embodiment 2

(i). The sample was an asymmetric SS-316L stainless steel membrane sheet (diameter, 30 mm; thickness, 2 mm), which was composed of a fine-porous layer with a thickness of ca. 200 μm and a macroporous support. The sample was cleaned successively with diluted HCl solution (HCl 37%, 1 ml/L), NaOH solution (0.5 mol/L) and water, each for about 5 min, followed by drying.

Figure 5:
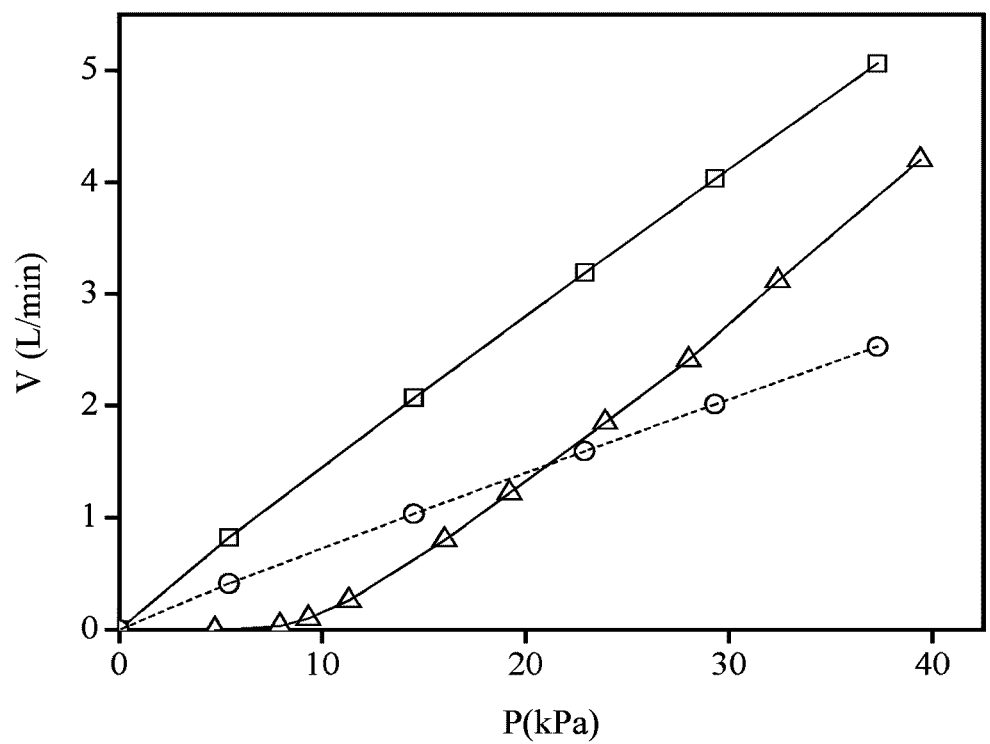
FIG. 5 shows the gas flux vs. pressure curves for an asymmetric stainless steel membrane.

(ii). The fine-porous membrane surface was measured. The dry, half-dry and wet curves were obtained following the same procedure as described in Steps (ii), (iii) and (iv) in Embodiment 1, and the results are shown in FIG. 5. The measured mean and largest pore-mouth sizes were 13.9 and 62.1 μm, respectively. For reference, the mean and largest pore-throat sizes were 9.1 and 41.7 μm, respectively.

Embodiment 3

(i). The sample was the same as that in Embodiment 2, but the surface of the macroporous support was measured this time.

Figure 6:
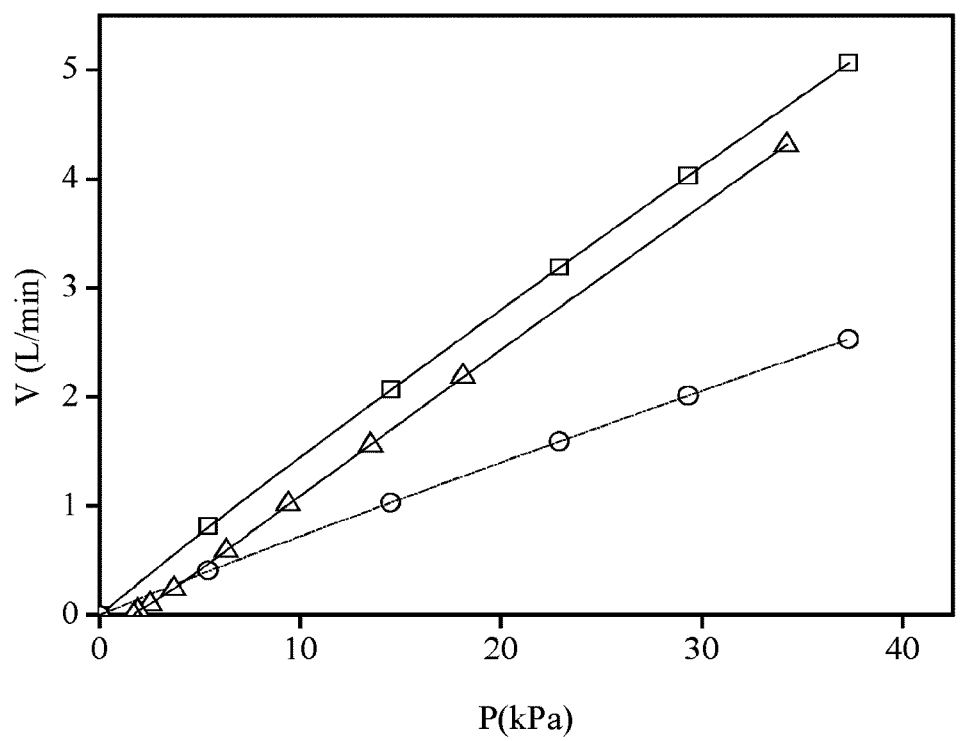
FIG. 6 shows the gas flux vs. pressure curves for the backside of the asymmetric stainless steel membrane. —☐—, Dry curve; —△—, Wet curve; —⊙—, Half-dry curve.

(ii). All other procedures were the same as those in Embodiment 2. The results are shown in FIG. 6. The mean and largest pore-mouth sizes were 64.8 and 171.5 μm, respectively.

(iii). The results in Embodiments 2 and 3 show that the pore-mouth size of the surface of the macroporous support is indeed much larger than that corresponding to the fine porous membrane surface, confirming the validity of the method described in this invention.

Embodiment 4

(i). The sample to be tested was a porous stainless steel sheet with a diameter of 30 mm and a thickness of 1.5 mm. The pre-treatment was the same as that in Step (i) of Embodiment 2.

(ii). This step was the same as Steps (ii), (iii) and (iv) in Embodiment 1 except that ethanol was employed as a wetting agent ($\gamma=22.3\times10^{-3}$ N/m). The mean and largest pore-mouth sizes were 4.9 and 12.1 μm, respectively.

(iii). The step was the same as Step (v) in Embodiment 1, but the wetting agent was Porewick, which was purchased from PMI Inc. The mean and largest pore-throat sizes obtained were 0.82 and 5.16 μm, respectively.

Embodiment 5

(i). The sample was a tubular porous stainless steel filter element (length, 10 mm; o.d., 12 mm; i.d., 9 mm) with mean and largest pore-throat sizes of 4.8 and 7.0 μm, respectively.

Figure 3:
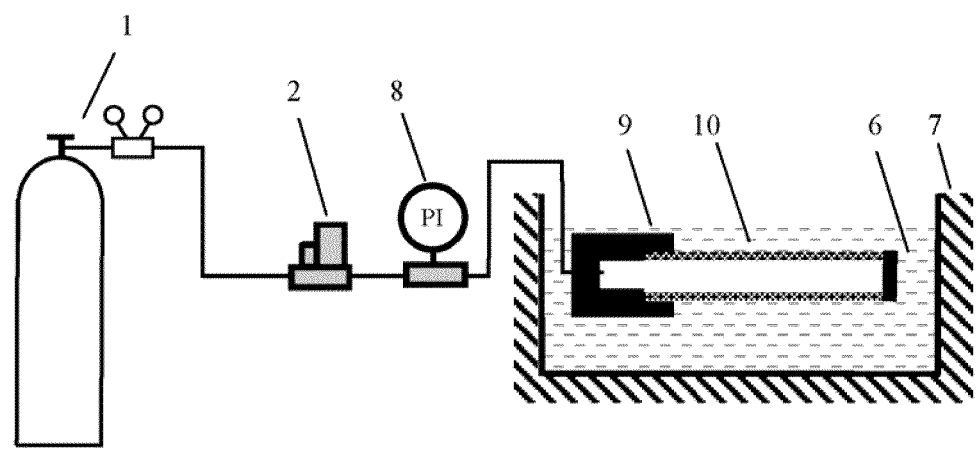
FIG. 3 shows a testing device for tubular samples. 1. Gas cylinder, 2. Mass flowmeter, 6. Wetting agent, 7. Tank, 8. Pressure controller, 9. Testing cell, 10. Sample.

(ii). The testing device, as shown in FIG. 3, consisted of a nitrogen gas cylinder (1), a mass flowmeter (2), a pressure controller (8), a testing cell (9), and a tank (7). One end of the sample (10) was blocked, and the other end was connected with the system. With an increase in the nitrogen pressure via the pressure controller (3), the nitrogen flowrate was recorded until the nitrogen pressure reached 100 kPa, which corresponded to a nitrogen flowrate of 2.2 L/min. The dry and half-dry curves were then plotted.

(iii). The water ($\gamma=72.9\times10^{-3}$ N/m) in the tank (7) was used as the wetting agent (6). The testing cell (9) was immersed 1-2 cm below the surface of the water (6), while the nitrogen pressure was regulated to 100 kPa through the controller. The testing cell (4) was slightly shaken so that the sample surface could sufficiently contact the water, and the flowmeter (2) read a value of 2 L/min. When the pressure in the system was decreased to 80 kPa, the nitrogen flowrate became 1.44 L/min. With a decrease in the nitrogen pressure, the nitrogen flowrate was recorded. When the bubbling pores became very few, the nitrogen was completely switched off, and the final pressure in the system (i.e., the "bubble point" pressure) was 10.1 kPa, which corresponded to the largest pore-mouth size of 28.9 μm. The wet curve was plotted, and the intersection point of the wet and half-dry curves corresponds to a pressure of 40.0 kPa, providing a mean pore-mouth size of 7.3 μm according to Eqn. [2].

What is claimed is:

1. A method for determination of the pore-mouth size distribution on the surface of porous materials, comprising the following steps. (i) While the backside of the sample is purged with a gas, the sample is immersed into a liquid wetting agent. (ii) Progress is monitored by either gradually decreasing the gas pressure and monitoring the gas flowrate or gradually decreasing the gas flowrate and monitoring the gas pressure. (iii) When the gas flow stops, the remaining pressure in the system corresponds to the largest pore-mouth size. (iv) The pore-mouth size distribution can be calculated through a "dry curve" and a "wet curve", which are curves of the gas flowrate vs. pressure at the dry and wetted states of the sample. (v) The mean pore-mouth size can be calculated by the pressure that corresponds to the intersection point between the "wet curve" and the "half-dry curve", wherein the "half-dry curve" is plotted with the data of the "dry curve" but halving each flowrate value.

2. In the method for the determination of the pore-mouth size distribution of porous materials according to claim 1, the porous materials can be ceramics, glasses, metals, plastics, or their composites.

* * * * *